United States Patent [19]
Sasagawa et al.

[11] Patent Number: 4,732,765
[45] Date of Patent: Mar. 22, 1988

[54] SUSTAINED RELEASE COATING COMPOSITION AND PREPARATION COATED THEREWITH

[75] Inventors: Tsutomu Sasagawa, Shizuoka; Toshiaki Sakashita, Hino; Toshio Honma, Hachioji, all of Japan

[73] Assignee: Toyo Jozo Co., Ltd., Tagata, Japan

[21] Appl. No.: 812,522

[22] Filed: Dec. 23, 1985

[30] Foreign Application Priority Data

Dec. 25, 1984 [JP] Japan .................................. 59-281663

[51] Int. Cl.⁴ .............................................. A61K 9/70
[52] U.S. Cl. ........................................ 424/476; 427/3; 427/212; 106/243; 428/403
[58] Field of Search ...................... 427/3, 212; 424/476

[56] References Cited

U.S. PATENT DOCUMENTS

| | | | |
|---|---|---|---|
| 2,205,111 | 6/1940 | Volwiler et al. | 424/476 |
| 3,184,386 | 5/1965 | Stephenson | 424/476 |
| 3,254,596 | 4/1966 | Lach | 427/476 |
| 3,256,153 | 6/1966 | Heimlich | 424/476 |
| 4,341,563 | 7/1982 | Kurihara et al. | 424/476 |

FOREIGN PATENT DOCUMENTS 747914  4/1956  United Kingdom ................ 424/476

Primary Examiner—Thurman K. Page
Assistant Examiner—L. R. Horne
Attorney, Agent, or Firm—Oblon, Fisher, Spivak, McClelland & Maier

[57] ABSTRACT

A sustained release coating composition, comprising a mixture of from 0.5–10 parts by weight of a metallic soap per 100 parts by weight of a higher alcohol.

4 Claims, 7 Drawing Figures

SUSTAINED RELEASE COATING COMPOSITION AND PREPARATION COATED THEREWITH

BACKGROUND OF THE INVENTION

1. Field of the Invention

The present invention relates to a sustained release coating composition and a preparation coated therewith, and more particularly to a sustained release coating composition containing a higher alcohol and a metallic soap, as well as to a sustained release coated preparation obtained by coating a core material, which contains an amino acid, vitamin, carbohydrate, antibiotic, antibacterial substance, steroid, anthelmintic or the like as its principal ingredient, with the coating composition.

2. Discussion of the Background

It is well known that coatings are applied to drugs in order to improve the appearance of the resulting pharmaceutical products, and therefore to increase the value of the drugs as commercial goods. Developments which have come about include the application of coatings to mask the unpleasant tastes, odors and the like of pharmaceutical products and/or to facilitate the administration of such pharmaceutical products. Further developments in the coating of drugs has been directed to the application of coatings to stabilize pharmaceutical products or to adjust and control the development of their efficacy as drugs. Moreover, coatings have found utility, for example, in the production of enteric preparations, sustained release preparations, repeat action type preparations and so on.

Not many methods, however, have been proposed with the objective of applying coatings to powders on an industrial scale. Although the known atomizer coating method makes use of a higher fatty acid or glycerin-fatty acid ester as a coating material (see, Japanese patent publication No. 13192/1975) and, other coating methods such as the roll coating method and micro-encapsulation method have been used to coat powders, none of these methods are satisfactory.

Coated preparations are generally required to have not only prompt release properties, in view of the stability of drugs, but also long-lasting release properties from the standpoint of adjustment and control of development of the efficacy of the drugs. Release patterns have been designed by taking these two requirements into parallel consideration. In fact, some coated preparations have been produced under conditions which take into account these two release patterns.

Although the conventional atomizer coating method is advantageous from the standpoint of production costs, it is accompanied by such drawbacks that the release patterns of the resulting coated preparations are constant and the preparations suffer from poor release properties when glycerine-fatty acid esters such as hydrogenated oil are employed as coating materials. Another factor is that limitations are imposed on applicable drugs when higher fatty acids are used as coating materials, because such higher fatty acids are reactive to basic drugs. Attempts have also been made to accelerate the release velocities of drug preparations by incorporating a surfactant such as sucrose-fatty acid ester or propylene glycol-fatty acid ester into the coating formulations with a view toward making improvements in the release properties of such coated drugs (see, Japanese patent publication No. 48050/1982; Japanese patent Laid-Open No. 28441/1984). However, the methods of release which are based upon release control of core materials by the action of surfactants are accompanied by several shortcomings which include the following: (1) Although surfactants having high HLBs are desirable from the viewpoint of release velocities, surfactants may, in many instances, fail to form homogeneous melts with coating materials such as oils and/or fats and tend to separate from the coating materials unless they have low HLBs. (2) Although it is desired that the coating materials which are employed in the atomizer coating method have certain degrees of melting readiness, for example, melting points on the order of 50–80° C., from the viewpoint of work efficiency and the storage of coated preparations, the addition of surfactants results in the reduction of the melting points of the coating materials or in the formation of coating films having reduced strength. (3) The amount of surfactant which is added to the coating formulation must be limited to such low levels that no significant improvement in release velocity is expected.

On the other hand, the coating materials which are required in the roll coating method, the micro-encapsulation method and the like, such as cellulose acetate phthalate, ethylcellulose, polyvinylacetal diethyl aminoacetate, are costly. Furthermore, these methods require the use of an organic solvent during production of the preparations and are thus troublesome to carry out. All of these factors just discussed increase the coats of production. A need therefore continues to exist for improved coating formulations for drug preparations.

SUMMARY OF THE INVENTION

Accordingly, an object of the present invention is to provide a coating formulation for a core material which provides for variable sustained release properties.

Another object of the present invention is to provide a coating composition which is particularly suitable for the coating of a finely powdered core material.

Briefly, these objects and other objects of the present invention as hereinafter will become more readily apparent can be attained by a sustained release coating composition which is a mixture of from 0.5-10 parts by weight of a metallic soap per 100 parts by weight of a higher alcohol.

Another embodiment of the present invention is a coated composition in which the coating formulation described above is applied to a core material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 2:
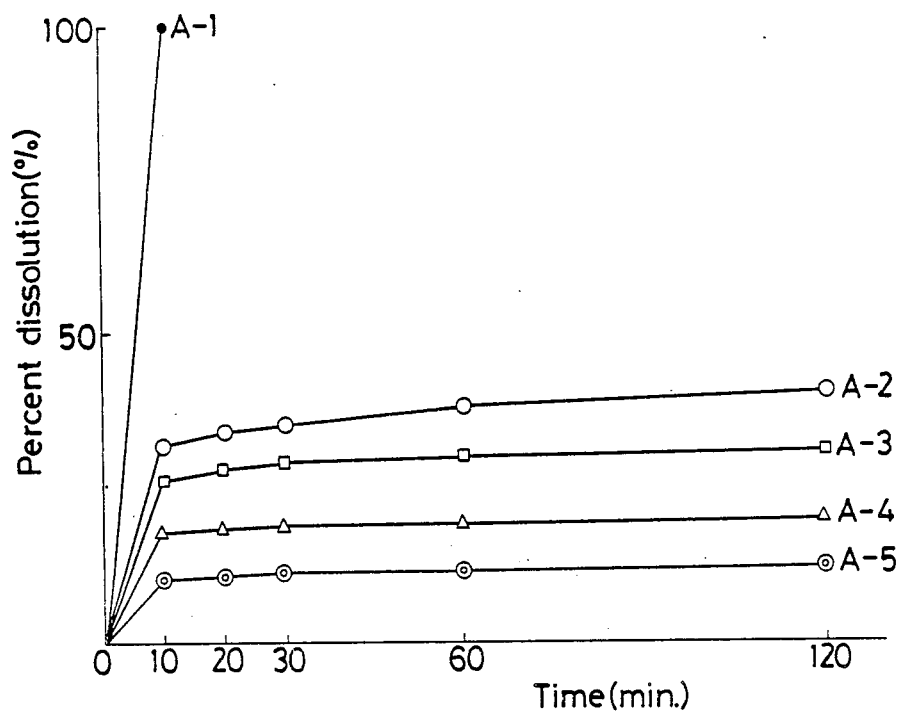
FIG. 2 is a graph which shows the variation of percent dissolution of DL-methionine particles coated with a cetanol-aluminum stearate formulation over time.

In the research conducted to find a way of overcoming the problems existing with the conventional methods of coating drug preparations, it has been found that a higher alcohol is more suitable as a base material in a coating formulation for use in the atomizer coating method from the viewpoint of its release properties than a hydrogenated oil. It has further been found that preparations coated with a coating formulation, which contain a higher alcohol in combination with a small amount of a metallic soap added thereto, have good sustained release properties.

It has also been found that even though higher alcohols generally have low melting points, these melting points are not lowered too much even by the addition of a metallic soap to the coating formulation, but on the contrary, the melting points actually increase depending on the amount of the metallic soap added to the coating formulation, and the efficiency of the atomizing process is improved in comparison to the way the atomization process proceeds when the higher alcohol is used alone. The presence of the metallic soap results in coating films which have higher strength, and coated preparations can be obtained with desired release patterns by changing the composition of the coating formulation and/or the thickness of the coating films.

The higher alcohols which are used in the practice of the present invention are those which are capable of providing coating compositions, the melting points of which, are suitable for atomizing work, for example, 50°-80° C. Saturated alcohols containing 12-28 carbon atoms are preferred. Suitable such alcohols include, for example, stearyl alcohol, lauryl alcohol, myristyl alcohol, cetanol and the like. Of these alcohols, stearyl alcohol and cetanol are particularly preferred because of their low costs. They also may be used singly or in combination.

On the other hand, the metallic soap component of the present formulation must form homogeneous melts with the above-described higher alcohols. Metal salts of aliphatic monocarboxylic acids containing 12-22 carbon atoms are preferred. Suitable monocarboxylic acids include, for example, lauric acid, myristic acid, palmitic acid, palmitoleic acid, stearic acid, oleic acid, linoleic acid, linolenic acid and the like. Commercial products such as aluminum soap, calcium soap, magnesium soap, zinc soap and the like may also be used as the metal soap component. These soaps may be used singly or in combination.

In the sustained release coating composition of the present invention, the amount of the metallic soap combined with the higher alcohol preferably ranges from 0.5-10 parts per 100 parts of the higher alcohol. If the metallic soap is combined in any amount greater than the above-stated upper limit, the resulting coating composition will have a greater increased viscosity which makes it unsuitable for atomizing work. Any amount smaller than the above-stated lower limit and the coating composition will also not be sufficient for use. The sustained release coating composition of the present invention can be produced by melting and mixing the higher alcohol and metallic soap.

Suitable core materials which can be used in combination with the coating of the invention to prepare a coated preparation within the scope of the present invention include biologically-effective materials and substances for humans and animals such as amino acids including methionine, lysine, tryptophan, and the like; vitamins including vitamin A palmitate, vitamin $B_1$, $B_2$, $B_6$, $B_{12}$, C, $D_3$ and E, nicotinamide, calcium pantothenate, choline, and the like; carbohydrates including glucose, fructooligosaccharides, and the like; antibiotics including ampicillin, chloramphenicol, chlorotetracycline, or oxytetracycline, and the like; synthetic antibacterial agents including sulfur drugs, thiamphenicol, carbadox, olaquindox, and the like; anthelmintics including piperazine salts, negphon, levamisole, thiabendazole, and the like; and steroid preparations including cortisone, predonisolone, dexamethasone, and the like. Two or more biologically-effective materials or substances in admixture may also be used. When coating the core material by the atomizing method, the core material is preferably in the form of fine powder, with a particle size of 10 μm or smaller being particularly preferred. When the core material has a large particle size, it preferably should be ground to a smaller particle size by an impact mill or the like before use.

In the practice of the present invention, the core material is preferably coated with the sustained release coating composition of the invention in an amount of 1-10 times by weight, notably, 2-4 times by weight the core material. If the amount of the coating composition is smaller than one times by weight, its coating effect cannot be exerted to any significant extent. On the other hand, even if the coating composition is used in any amount in excess of 10 times by weight, no significant additional effects are obtained as a result of the greater amount of coating agent employed. Moreover, the use of greater quantities of coating material only increases material costs.

Since the sustained release coating composition of the present invention permits the release of the core material over a longer period of time and provides coating films which have greater strength and are less susceptible to rupture under physical stress as the proportion of the metallic soap ingredient increases, a greater or lesser amount of metallic soap ingredient is employed in the coating composition depending upon the release pattern designed for a given mode of administration or stabilization of the core material. When the coating composition is used, for example, in an amount 2-3 times by weight the core material, it is most preferred to incorporate the metallic soap in the composition in an amount of 2 wt. % or so based on the higher alcohol component from the viewpoint of controlling the working efficiency, physical characteristics, and the release and longacting properties of the core material. When the coating composition is used in an amount of 1-1.5 times by weight the core material, in other words, when the core material is used in a large amount, the metallic soap is preferably used in a larger amount relative to the higher alcohol. For example, 5-10 wt. % is especially preferred.

When the atomizing method of coating is employed to coat material, the coating preparation of the invention can be conveniently prepared by melting and mixing the higher alcohol and metallic soap ingredients at a temperature of about 90°-130° C., and then adding the core material to the melt. The resultant mixture is evenly dispersed, and by use of a rotary disk type spray drier or the like (hereinafter called "atomizer" collectively), the thus-prepared dispersion is atomized preferably at 90°-95° C. in a room whose temperature is controlled below 30° C. If the core material has poor thermal stability, the atomization of the dispersion is preferably conducted at a temperature, which is somewhat lower than the above-employed temperature. However, the viscosity of the dispersion can be prevented from undergoing a considerable increase, by increasing the speed of revolution of the atomizer cup. In a preferred method of operation the atomization process is conducted by increasing the speed of revolution of the atomizer cup when the core material is used in a large amount. The thus-obtained powder is mixed with an anti-caking agent (dusting powder) subsequent to the atomization as needed. Suitable anti-caking agents include ultra-light synthetic aluminum silicate, light calcium carbonate, and the like. Preferably, the product coating preparation is subjected to classification by sieving.

The sustained release coating composition of the present invention, which contains the higher alcohol and metallic soap, is effective in controlling the dissolubility of the core material which it coats. Moreover, this effect can be controlled by changing the proportion of the metallic soap incorporated in the coating composition. For example, the dissolubility of the core material can be reduced in order to improve its longacting properties by increasing the proportion of the metallic soap in the coating.

The use of the coating composition of the present invention permits the production of a coated preparation which has a release pattern designed for the specific dissolubility desired for the biologically-effective substance coated. The coating preparation of the present invention is particularly useful for the coating of bovine drugs which are used in the recently developed teachinque of drug delivery in which a coated drug is allowed to pass through the rumen without the drug being affected by bacteria in the rumen or without the drug itself affecting bacteria in the rumen. Another area of particular applicability is the stabilization of vitamin $B_1$ in order to avoid degradation of the vitamin by thiaminase in minced raw fish feed which is used in fish farming.

Having generally described this invention, a further understanding can be obtained by reference to certain specific examples which are provided herein for purpose of illustration only and are not intended to be limiting unless otherwise specified.

EXAMPLE 1

Using the higher alcohols and metallic soaps shown in Table 1, sustained release coating compositions of the present invention were prepared and their physical properties were investigated. The results are shown in Table 1. The hardness values obtained measured by melting and then solidifying the compositions, followed by cutting the material into rectangular blocks 10 mm × 10 mm × 6 mm in size. The hardness of the material was measured by means of a Kiya-type hardness meter. Table 1 also shows certain physical properties of the higher alcohols and metallic soaps, which were used the as raw materials, as well as comparative products.

TABLE 1

| | Sustained release coating composition* | | Melting point (°C.) | Solidifying point (°C.) | Hardness (kg) |
|---|---|---|---|---|---|
| CONTROL | Stearyl alcohol | | 55-56 | 56-55 | 2.6 |
| | Cetanol | | 49-50 | 50-49 | 3.0 |
| | Hardened castor oil | | 80-84 | 83-80 | 6.0 |
| | Hardened beef tallow | | 60-61 | 59-57 | 5.4 |
| | Aluminum stearate | | 110-125 | — | — |
| | Magnesium stearate | | 110-135 | — | — |
| | Calcium stearate | | 150-160 | — | — |
| | Zinc stearate | | 116-124 | — | — |
| Invention | Stearyl alcohol + aluminum stearate | 1% | 58-60 | 59-58 | 5.8 |
| | Stearyl alcohol + aluminum stearate | 2% | 57-58 | 55-53 | 6.4 |
| | Stearyl alcohol + aluminum stearate | 3% | 56-57 | 55-53 | 6.5 |
| | Stearyl alcohol + aluminum stearate | 5% | 54-56 | 50-49 | 7.2 |
| | Stearyl alcohol + aluminum stearate | 10% | 54-56 | 50-49 | 7.5 |
| | Stearyl alcohol + magnesium stearate | 3% | 67-68 | 60-59 | 5.0 |
| | Stearyl alcohol + magnesium stearate | 5% | 74-75 | 72-70 | 5.5 |
| | Stearyl alcohol + magnesium stearate | 10% | 74-75 | 72-69 | 5.9 |
| | Stearyl alcohol + calcium stearate | 5% | 74-75 | 64-67 | 5.8 |
| | Stearyl alcohol + zinc stearate | 5% | 74-75 | 78-76 | 5.4 |
| | Cetanol + aluminum stearate | 2% | 55-56 | 50-49 | 5.6 |
| | Cetanol + aluminum stearate | 5% | 56-57 | 48-47 | 7.0 |
| | Cetanol + aluminum stearate | 10% | 56-57 | 48-47 | 7.2 |

*Numerals indicate the proportions of the metallic soaps mixed with the corresponding higher alcohols.

As is apparent from Table 1, the sustained release coating compositions of the present invention have melting points which are either equal to or somewhat higher than the starting raw materials. Thus, the higher alcohols shown are suitable for the atomizing method. It has also been found that the hardness of the coating compositions increases as the amount of the added metallic soap increases.

EXAMPLE 2

As described below, a coated thiamine nitrate product was produced using a coating composition which was composed of cetanol and aluminum stearate.

A 7.35 kg amount of cetanol was mixed with 150 g of aluminum stearate. After heating and stirring the resulting mixture at 120° C. to form a homogeneous melt, the melt was cooled to 80° C. Thereafter, 2.5 kg of ground thiamine nitrate was added to the melt and uniformly dispersed in the melt which was maintained at 80° C.

While maintaining the resultant molten mixture in the heated state, it was introduced into a high-speed rotary disk parallel-downflow type spray drier (height: 4.85 m; cylinder diameter: 2.5 m) and was then atomized at 5,400 rpm. The atomization was carried out while being cooled with air having a temperature of 25° C. and an atomization capacity of 1–2 kg/min. After atomization and cooling, the thus-obtained powder was passed through a sieve of 24 mesh, followed by the addition of 10 g of light silicon dioxide to avoid caking of the product. A coated thiamine nitrate product was thus obtained.

In the manner described above, except for changes in the amounts of aluminum stearate and cetanol employed, other coated thiamine nitrate samples were prepared which are also shown in Table 2.

TABLE 2

| Coated thiamine nitrate | A-1 | A-2 | A-3 | A-4 | A-5 |
|---|---|---|---|---|---|
| Formulation (kg) | | | | | |
| Thiamine nitrate | 2.5 | 2.5 | 2.5 | 2.5 | 2.5 |
| Coating material Cetanol | — | 7.5 | 7.425 | 7.35 | 7.275 |
| Aluminum stearate | — | — | 0.075 | 0.15 | 0.225 |
| Conditions for production | | | | | |
| Particle size of the core material | 10 μm or smaller | 10 μm or smaller | | | |
| Heating and melting temperature of coating materials | | | 120° C. | | |
| Atomizing temperature | | | 80° C. | | |
| Cooling air temperature | | | 25° C. | | |
| Revolution speed of atomizer | | | 5,400 rpm | | |

EXAMPLE 3

The coated DL-methionine samples in Table 3 were produced in the same manner as the procedure described in Example 2, except that DL-methionine was used in place of thiamine nitrate. Since DL-methionine is colored at temperatures above 80° C., it must be mixed at a temperature less than 80° C. Thus, the atomizing temperature of the atomizer was set at 75° C.

TABLE 3

| Coated DL-methionine | B-1 | B-2 | B-3 | B-4 | B-5 |
|---|---|---|---|---|---|
| Formulation (kg) | | | | | |
| DL-methionine | 2.5 | 2.5 | 2.5 | 2.5 | 2.5 |
| Coating material | | | | | |
| Cetanol | — | 7.5 | 7.425 | 7.35 | 7.275 |
| Aluminum stearate | — | — | 0.075 | 0.15 | 0.225 |
| Conditions for production | | | | | |
| Particle size of the core material | 10 μm or smaller | 10 μm or smaller | | | 10 μm or smaller |
| Heating and melting temperature of coating materials | | | 120° C. | | 120° C. |
| Atomizing temperature | | | 75° C. | | 75° C. |
| Cooling air temperature | | | 25° C. | | 25° C. |
| Revolution speed of atomizer | | | 5,400 rpm | | 7,400 rpm |

EXAMPLE 4

The coated ampicillin samples shown in Table 4 were produced in the same manner as described in Example 2, except that 2.95 g of ampicillin.3 H$_2$O was used in lieu of 2.5 g of thiamine nitrate, and the amounts of the coating materials were changed. Incidentally, ampicillin.3 H$_2$O has an antibiotic potency of 250 g/295 g (850 mg antibiotic potency/g). Since ampicillin is unstable to heat, mixing and atomization were carried out at temperatures as low as feasible. In addition, the heating time was shortened as much as possible.

TABLE 4

| Coated ampicillin | C-1 | C-2 | C-3 | C-4 | C-5 |
|---|---|---|---|---|---|
| Formulation (kg) | | | | | |
| Ampicilline.3 H$_2$O | 2.95 | 2.95 | 2.95 | 2.95 | 2.95 |
| Coating Cetanol | — | 7.05 | 6.98 | 6.91 | 6.84 |
| material Aluminum stearate | — | — | 0.07 | 0.14 | 0.21 |
| Conditions for production | | | | | |
| Particle size of the core material | 10 μm or smaller | 10 μm or smaller | | | |
| Heating and melting temperature of coating materials | | | 120° C. | | |
| Atomizing temperature | | | 70° C. | | |
| Cooling air temperature | | | 25° C. | | |
| Revolution speed of atomizer | | | 7,400 rpm | | |

EXAMPLE 5

Figure 3:
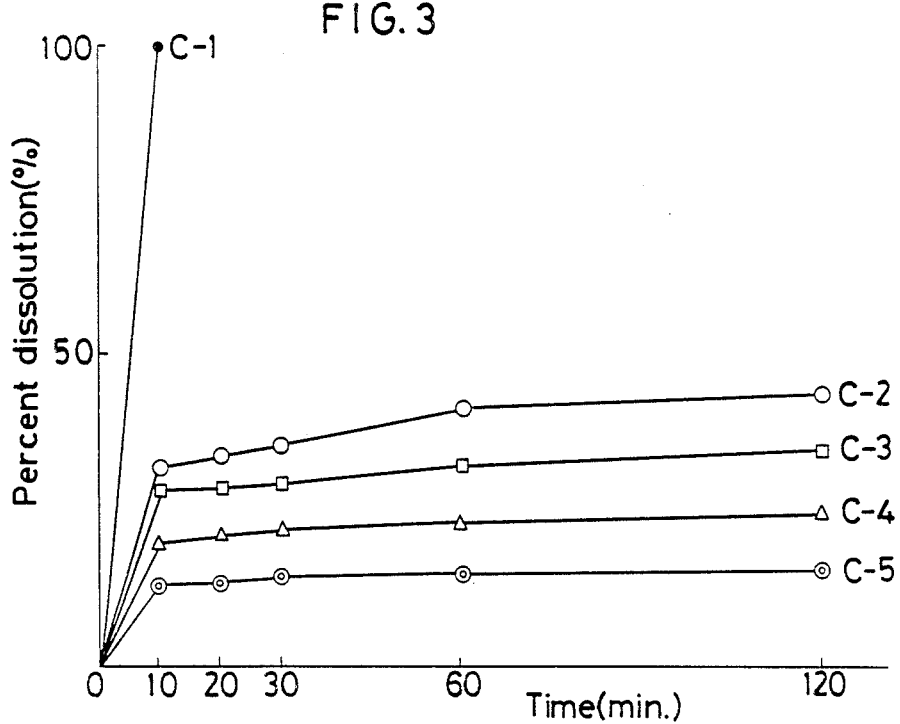
FIG. 3 is a graph which shows the variation of percent dissolution of ampicillin particles coated with a cetanol-aluminum stearate formulation over time.

Dissolution tests were carried out on the coated thiamine nitrate samples, DL-methionine samples and ampicillin samples which were produced in Examples 2–4 respectively, by the method described below. Test results are shown in Table 5 and FIGS. 1 through 3.

(1) Dissolution Method:

The dissolution testing method 2 disclosed in "The Pharmacopoeia of Japan", tenth edition (J.P. X) (the paddle method) was employed with the apparatus described therein. The tests were conducted at 37±0.5° C. Dissolved solutions were sample 10, 20, 30, 60 and 120 minutes later using 0.01 N-HCl. The amounts of thiamine nitrate, DL-methionine and ampicillin which had dissolved in the filtrates were quantitatively analyzed by the following methods (2).

(2) Quantitative Analyses:

Thiamine nitrate: The modified cyanogen bromide cytochrome fluorescence analysis.

DL-methionine: The modified Lavin method ["The Pharmacopoeia of Japan", eighth edition (J. P. VIII)]

Ampilicillin: Diluted with phosphate buffer.
Test bacterium: *Bacillus subtilis* ATCC 6633.
Method: Cylinder assay.

TABLE 5

| | Percent dissolution (%) | | | | |
|---|---|---|---|---|---|
| Sample | 10 min. later | 20 min. later | 30 min. later | 60 min. later | 120 min. later |
| A-1 | 100 | — | — | — | — |
| A-2 | 32.4 | 34.2 | 35.1 | 38.1 | 40.7 |
| A-3 | 26.2 | 28.3 | 29.0 | 30.2 | 31.6 |
| A-4 | 17.7 | 18.2 | 18.6 | 19.0 | 20.2 |

TABLE 5-continued

| Sample | Percent dissolution (%) | | | | |
|---|---|---|---|---|---|
| | 10 min. later | 20 min. later | 30 min. later | 60 min. later | 120 min. later |
| A-5 | 10.4 | 10.8 | 11.1 | 11.6 | 12.3 |
| B-1 | 100 | — | — | — | — |
| B-2 | 29.6 | 31.0 | 31.8 | 32.4 | 32.9 |
| B-3 | 21.7 | 22.6 | 22.9 | 23.3 | 23.7 |
| B-4 | 14.2 | 14.5 | 14.7 | 15.0 | 15.2 |
| B-5 | 10.1 | 10.3 | 10.4 | 10.6 | 10.6 |
| C-1 | 100 | — | — | — | — |
| C-2 | 31.2 | 33.7 | 34.8 | 41.5 | 44.1 |
| C-3 | 27.8 | 28.6 | 29.2 | 32.4 | 35.0 |
| C-4 | 19.5 | 21.3 | 22.1 | 23.2 | 24.9 |
| C-5 | 12.4 | 13.1 | 13.7 | 14.3 | 15.1 |

EXAMPLE 6

The compositions shown in Table 6 were prepared in the same manner as described in Example 2, except that stearyl alcohol was used as the higher alcohol instead of cetanol, and magnesium stearate was employed as the metallic soap in place of aluminum stearate. Following the procedures described in Example 2, coated thiamine nitrate samples were produced. Dissolution tests were conducted on the samples in the same manner as described in Example 5. Test results are shown in Table 7 and FIG. 4.

TABLE 6

| Coated thiamine nitrate | D-1 | D-2 | D-3 |
|---|---|---|---|
| Formulation (kg) | | | |
| Thiamine nitrate | 5.0 | 5.0 | 5.0 |
| Coating material | | | |
| Stearyl alcohol | 4.85 | 4.75 | 4.50 |
| Magnesium stearate | 0.15 | 0.25 | 0.50 |
| Conditions for production | | | |
| Particle size of core materials | 10 μm or smaller | | |
| Heating and melting temperature of coating material | 120° C. | | |
| Atomizing temperature | 85° C. | | |
| Cooling air temperature | 25° C. | | |
| Revolution speed of atomizer | 7,400 rpm | | |

TABLE 7

| Sample | Percent dissolution (%) | | |
|---|---|---|---|
| | 10 min. later | 30 min. later | 60 min. later |
| D-1 | 48.32 | 72.11 | 91.48 |
| D-2 | 40.91 | 65.45 | 70.45 |
| D-3 | 38.64 | 57.49 | 66.45 |

Figure 4:
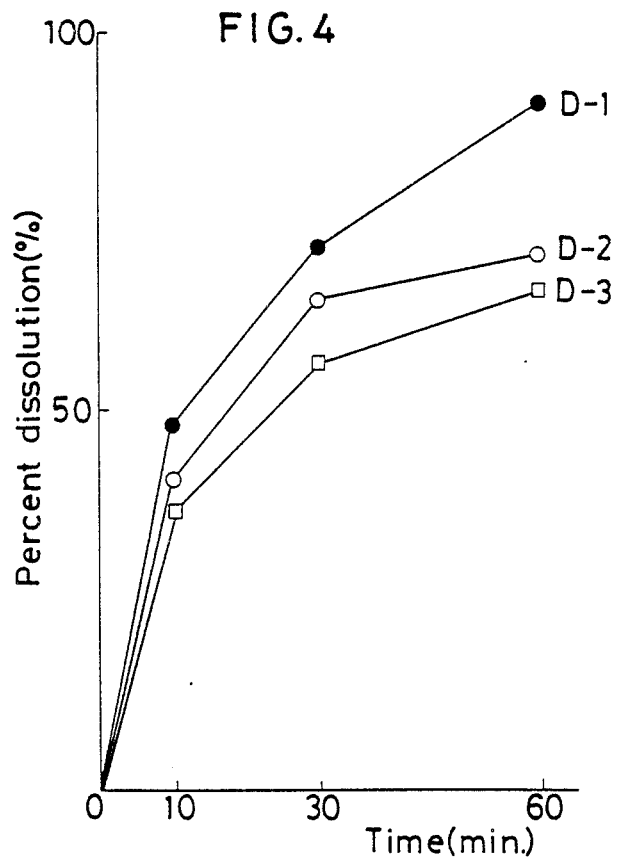
FIG. 4 is a graph which shows the variation of percent dissolution of thiamine nitrate particles coated with a stearyl alcohol-magnesium stearate formulation over time.

As is apparent from Table 7 and FIG. 4, the percent dissolution of thiamine nitrate decreases in the formulation shown in Table 6 as the content of the metallic soap increases.

EXAMPLE 7

The stabilities of coated thiamine nitrate samples, which were prepared from the coating formulation shown in Table 8 by the procedure described in Example 2, except that cetanol was replaced by stearyl alcohol, in minced sardine (*Sardinops melanosticta*), and the concentrations of thiamine nitrate in blood (the blood level of the compound) upon the forced oral administration of the coated drug to young yellowtails (*Seriola quinqueradiata*) were investigated. The forced oral dosage was 50 mg/kg B.W. in terms of thiamine nitrate. Since it is impossible to collect blood periodically from young yellowtails, apparent blood levels were determined. The blood levels were then expressed in terms of the average value of blood levels in a group of five yellowtails. The results are shown in Tables 9 and 10 and FIGS. 5 and 6.

TABLE 8

| Coated thiamine nitrate | E-1 | E-2 | E-3 | E-4 | E-5 |
|---|---|---|---|---|---|
| Formulation (kg) | | | | | |
| Thiamine nitrate | 2.5 | 2.5 | 2.5 | 2.5 | 2.5 |
| Coating Stearyl alcohol | — | 7.5 | 7.425 | 7.35 | 7.275 |
| material Aluminum stearate | — | — | 0.075 | 0.15 | 0.225 |
| Conditions for production | | | | | |
| Particle size of the core material | 10 μm or smaller | 10 μm or smaller | | | |
| Heating and melting temperature of coating materials | 120° C. | | | | |
| Atomizing temperature | 80° C. | | | | |
| Cooling air temperature | 25° C. | | | | |
| Revolution speed of atomizer | 5,400 rpm | | | | |

TABLE 9

| Sample | Percent remainder of coated thiamine nitrate in minced sardine | | |
|---|---|---|---|
| | 0.5 hr. later | 1 hr. later | 2 hrs. later |
| E-1 | 28.4 | 23.2 | 15.0 |
| E-2 | 44.5 | 40.0 | 31.1 |
| E-3 | 56.3 | 56.0 | 44.8 |
| E-4 | 68.9 | 66.5 | 60.0 |
| E-5 | 82.5 | 76.0 | 74.6 |

Figure 5:
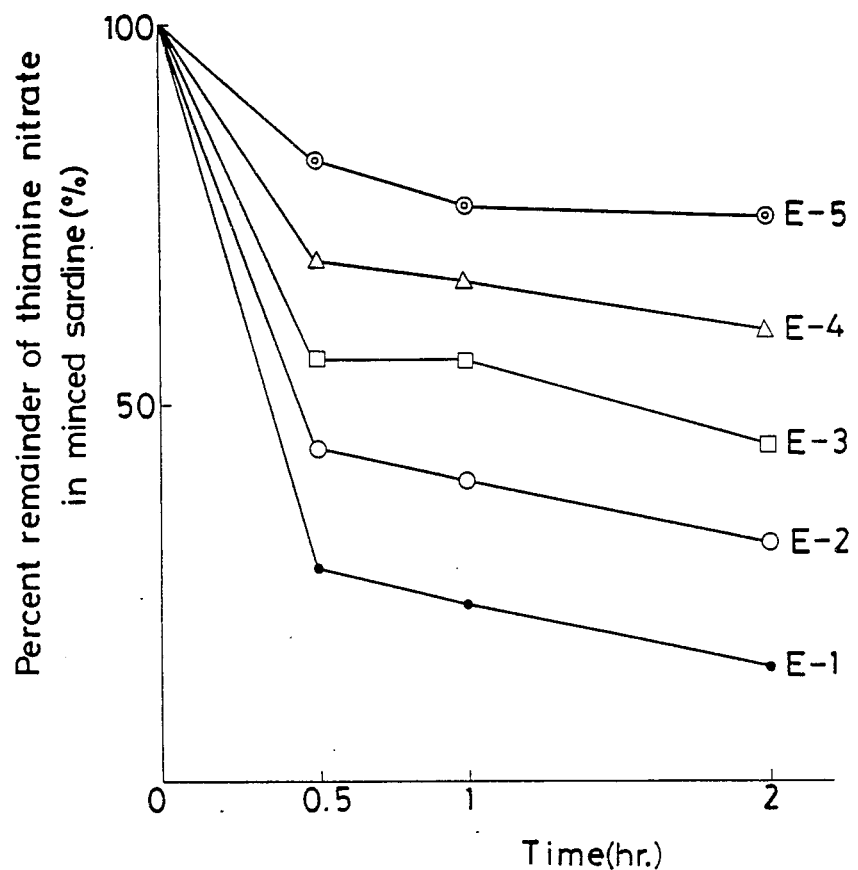
FIG. 5 is a graph which shows the percent of thiamine nitrate which remains in minced sardine with the passage of time from thiamine nitrate particles coated with stearyl alcohol-aluminum stearate formulation.

As can be readily seen from the data in Table 9 and FIG. 5, the stability of the coated drug was improved as the content of the metallic soap in the coating composition increased.

TABLE 10

| Sample | Blood level of thiamine nitrate in young yellowtail | | | | |
|---|---|---|---|---|---|
| | 0 hr. later | 1 hr. later | 3 hrs. later | 6 hrs. later | 12 hrs. later |
| E-1 | 104 | 382 | 215 | 127 | 103 |
| E-2 | 104 | 307 | 205 | 146 | 107 |
| E-3 | 104 | 251 | 221 | 152 | 103 |
| E-4 | 104 | 228 | 217 | 172 | 115 |
| E-5 | 104 | 186 | 185 | 169 | 108 |
| Control* | 104 | 122 | 152 | 168 | 114 |

*The control was thiamine nitrate coated with hydrogenated castor oil in place of the same amount of stearyl alcohol in sample E-2.

Figure 6:
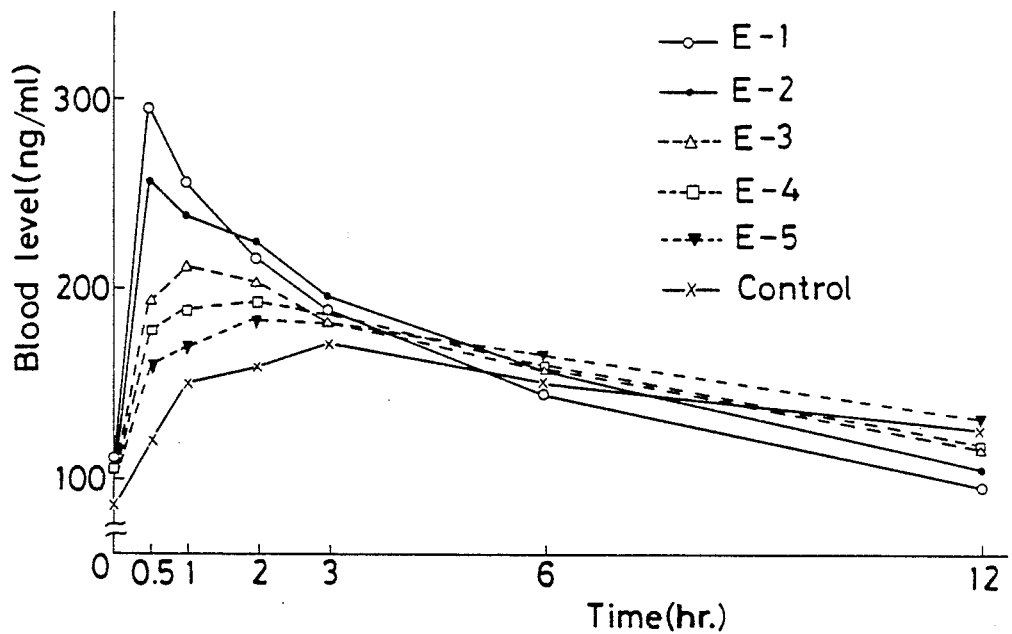
FIG. 6 is a graph which shows the variations in blood level of thiamine nitrate in young yellowtails with the passage of time when the drug is forcedly and orally administered to the young yellowtails.

As is apparent from the data in Table 10 and FIG. 6, the coated thiamine nitrate samples of the present invention were absorbed as promptly as the uncoated sample, E-1, and they were able to maintain high blood levels. On the other hand, the control product coated with hydrogenated castor oil showed lower blood levels and hence significantly inferior absorption.

EXAMPLE 8

As absorption test on coated thiamine nitrate samples obtained in the same manner as described in Example 7 by rabbits was carried out in the manner described below. The test results are given in Table 11 and FIG. 7.

(Testing method)

Six male rabbits (avarage body weight: 2.8 kg) were used per group. They were fasted except for drinking water for 18 hours before the test. The dosage of each coated thiamine nitrate sample was 50 mg/kg B.W. Each coated thiamine nitrate sample was administered by suspending the above dosage in a liquid and then the suspension was forcefully administered into the stomach through the mouth by means of a probe. Blood samples were collected from the otic veins. Blood levels were quantitatively analyzed by the modified permutite-cyanogen bromide-cytochrome fluorescence analysis technique. The test was conducted after the relationship between the oral dosage of thiamine nitrate and the blood level had been investigated in a preliminary test and as a result, the dose-response was observed to be in the range of 12.5–200 mg/kg B.W.

TABLE 11

| Sample | Blood Level (ng/ml) | | | | | | |
|---|---|---|---|---|---|---|---|
| | 0 hour later | 0.5 hour later | 1 hour later | 2 hours later | 3 hours later | 6 hours later | 12 hours later |
| E-1 | 97 | 295 | 256 | 217 | 190 | 146 | 95 |
| E-2 | 102 | 258 | 239 | 225 | 196 | 158 | 104 |
| E-3 | 111 | 194 | 211 | 204 | 183 | 160 | 115 |
| E-4 | 105 | 179 | 190 | 195 | 187 | 161 | 119 |
| E-5 | 108 | 161 | 171 | 183 | 181 | 165 | 131 |
| Control* | 86 | 120 | 151 | 159 | 172 | 151 | 126 |

*the same control product as that used in Example 7, Table 10.

Figure 7:
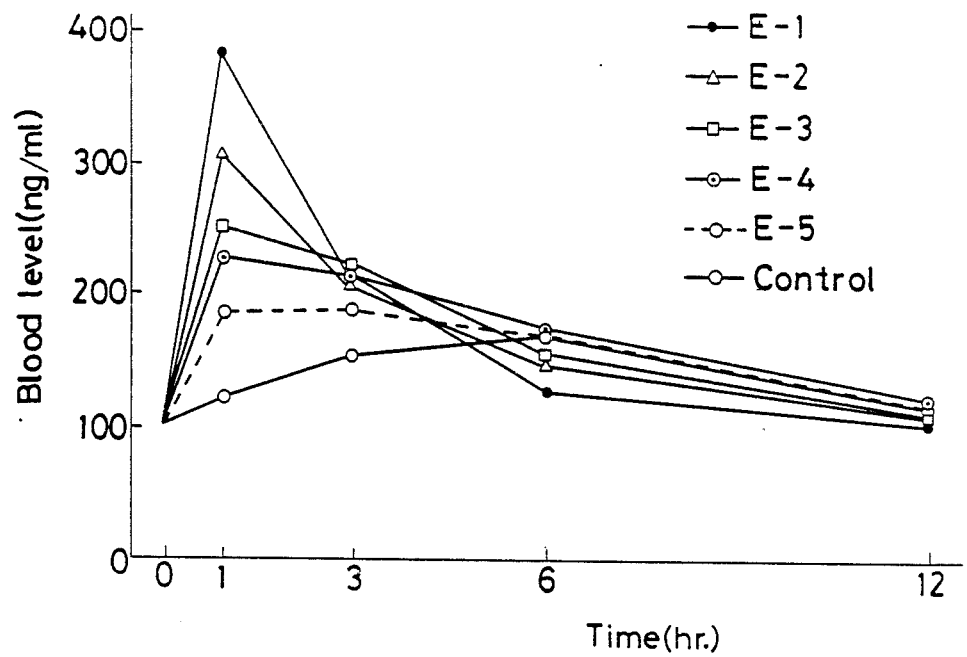
FIG. 7 is a graph which shows the variation in blood level of thiamine nitrate with the passage of time after coated thiamine nitrate is forcedly and orally administered to rabbits.

As apparent from the data in Table 11 and FIG. 7, the sample, E-2, obtained by using stearyl alcohol as the sole coating material showed substantially the same behavior as the uncoated sample, E-1, but the long-acting properties of the coated drug were enhanced as the amount of the aluminum stearate increased in the coating.

Having now fully described the invention, it will be apparent to one of ordinary skill in the art that many changes and modifications can be made thereto without departing from the spirit or scope of the invention as set forth herein.

What is claimed as new and is secured by letters patent is:

1. A core material coated with a sustained release coating composition comprising a mixture of from 0.5–10 parts by weight of a metallic soap derivant from an acid having 12–22 carbon atoms per 100 parts by weight of an higher having 12–28 carbon atoms alcohol, the amount of said coating composition ranging from 1–10 times by weight of the core material.

2. The coated composition of claim 1, wherein said core material is an amino acid, a vitamin, a carbohydrate, an antibiotic, a synthetic antibacterial agent, an anthelmintic or a steroid.

3. The coated composition of claim 1, wherein the particle size of the core material is no more than 10 μm.

4. The coated composition of claim 1, wherein the amount of said coating ranges from 2–4 times by weight of the core material.

* * * * *

UNITED STATES PATENT AND TRADEMARK OFFICE
CERTIFICATE OF CORRECTION

PATENT NO. : 4,732,765

DATED : March 22, 1988

INVENTOR(S) : Tsutomu Sasagawa et al.

Figure 1:
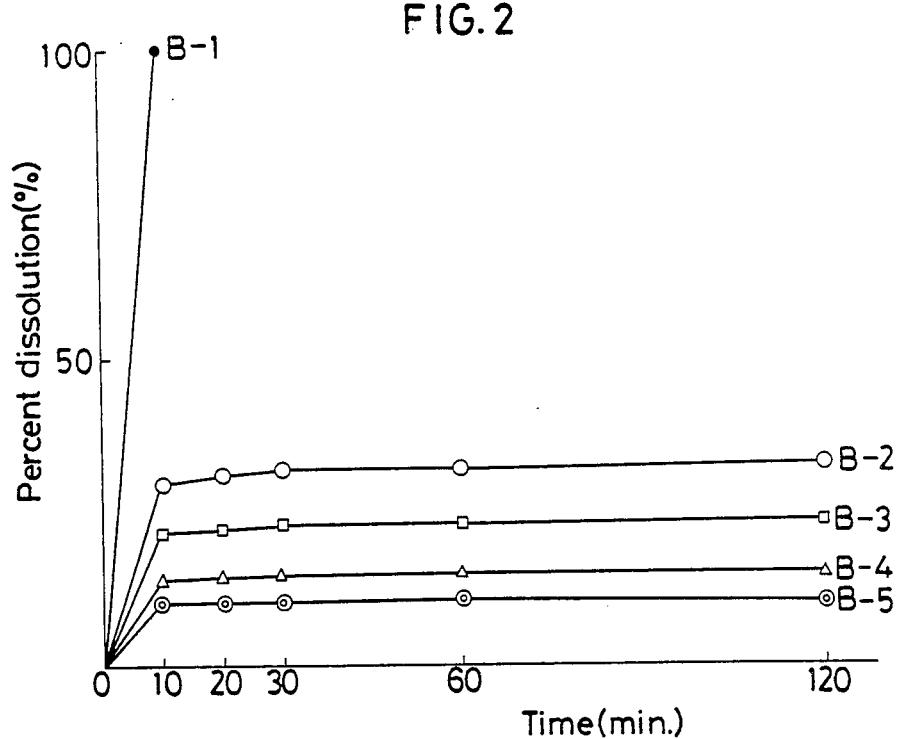
FIG. 1 is a graph which shows the variation of percent dissolution of thiamine nitrate particles coated with a cetanol-aluminum stearate formulation over time.

It is certified that error appears in the above-identified patent and that said Letters Patent is hereby corrected as shown below:

Insert -- FIG. 1 -- above the top figure of Sheet 1 of 4 of the drawing.

Insert -- FIG. 6 -- above the top figure of Sheet 4 of 4 of the drawing.

Signed and Sealed this

Thirteenth Day of September, 1988

Attest:

DONALD J. QUIGG

Attesting Officer

Commissioner of Patents and Trademarks